United States Patent [19]
Thenappan et al.

[11] Patent Number: 5,824,826
[45] Date of Patent: Oct. 20, 1998

[54] PROCESS FOR THE PREPARATION OF 1,1,2,3,3,4-HEXAFLUOROBUTANE

[75] Inventors: Alagappan Thenappan, Cheektowaga; Michael Van Der Puy, Amherst; Andrew J. Poss, Kenmore, all of N.Y.

[73] Assignee: AlliedSignal Inc., Morristown, N.J.

[21] Appl. No.: 883,931

[22] Filed: Jun. 27, 1997

[51] Int. Cl.$^6$ .................................................. C07C 21/18
[52] U.S. Cl. ........................................................ 570/134
[58] Field of Search .............................................. 570/134

[56] References Cited

U.S. PATENT DOCUMENTS 5,421,971  6/1995  Van Der Puy et al. ............. 204/157.6
5,696,307  12/1997  Van Der Puy et al. ................ 570/134

FOREIGN PATENT DOCUMENTS 0 431 458 A1  11/1990  European Pat. Off. .
6-212014  2/1994  Japan .
WO 95/19947  7/1995  WIPO .

OTHER PUBLICATIONS

English Abstract JP 6 212014 (1994).
International Search Report, 1995.

*Primary Examiner*—Zinna Northington Davis
*Attorney, Agent, or Firm*—Colleen D. Szuch; Jay P. Friedenson

[57] ABSTRACT

The invention provides a process for the preparation of 1,1,2,3,3,4-hexafluorobutane by telomerization of chlorotrifluoroethylene to produce 1,1,3,4-tetrachlorohexafluorobutane followed by reduction of that compound to 1,1,2,3,3,4-hexafluorobutane.

19 Claims, No Drawings

PROCESS FOR THE PREPARATION OF 1,1,2,3,3,4-HEXAFLUOROBUTANE

FIELD OF THE INVENTION

The invention relates to a process for the preparation of 1,1,2,3,3,4-hexafluorobutane. In particular, the process provides a method for preparing 1,1,2,3,3,4-hexafluorobutane by telomerization of chlorotrifluoroethylene to produce 1,1,3,4-tetrachlorohexafluorobutane followed by reduction of that compound to 1,1,2,3,3,4-hexafluorobutane.

BACKGROUND OF THE INVENTION

Hydrofluorocarbons ("HFC's") are of great interest due to their potential to replace ozone-depleting chlorofluorocarbons ("CFC's") in a variety of application including refrigerant, solvent, foam blowing agent, and aerosol propellant applications. Among the HFC's, 1,1,2,3,3,4-hexafluorobutane ("HFC-356pecq") has been disclosed as a cleaning and degreasing solvent in WO 95/19947. Japanese Patent Application No. 06212014 discloses the use of —$CHF_2$-containing, low-boiling HFC's of the formula $C_4F_6H_4$ as foam blowing agents in the manufacture of polyurethane foams. Aliphatic HFC's of the formula $C_nF_mH_{2n+2-m}$ in which n=4–6 and m=6–12, are disclosed as active ingredients in cleaning compositions to remove fats, fluxes, oils, and dust deposited on integrated circuit boards and precision instruments in EP 431 458.

Methods for producing HFC-356pecq are known. For example, HFC356pecq has been identified as one of 49 components in the fluorination of n-butane over cobalt trifluoride. Reductive dehalogenations of 1,1,3,4-tetrachlorohexafluorobutane ("CFC-3161bc") with tributyltin hydride to produce HFC-356pecq are also known. However, these processes are not practical on a commercial scale either due to the low yield of HFC-356pecq or the expense of the reagents used. Therefore, a need exists for a method to produce HFC-356pecq that is useful on a commercial scale.

DESCRIPTION OF THE INVENTION

The invention provides processes for the preparation of 1,1,2,3,3,4-hexafluorobutane, HFC-356pecq, amenable to large scale manufacturing. The processes of the invention may be conducted as either a batch or a continuous process to produce ETC-356pecq in high yields.

In one embodiment, the invention provides a process for producing HFC356pecq comprising the step of reducing CFC-316bc with hydrogen in the presence of catalytic amounts of a hydrogenation catalyst under conditions suitable to produce an HFC-356pecq product mixture comprising HFC-356pecq product. The CFC-3161bc is commercially available. Alternatively, the CFC-3161bc may be produced in high selectivity by telomerizing chlorotrifluoroethylene ("CFC-1113") using a solvent of the formula $C_4Cl_4F_6$.

Thus, in another embodiment of the invention, a process for producing CFC-3161bc is provided comprising telomerizing CFC-1113 with an effective amount of a telogen and in the presence of effective amounts of an initiator and a solvent of the formula $C_4Cl4F_6$, under conditions suitable to produce a CFC-3161bc product mixture comprising CFC-3161bc.

In a preferred embodiment, the invention provides a process for producing HFC-356pecq comprising the steps of telomerizing CFC-1113 with an effective amount of a telogen and in the presence of effective amounts of an initiator and a solvent of the formula $C_4Cl_4F_6$, under conditions suitable to produce a CFC-316bc product mixture comprising CFC-3161bc; recovering purified CFC-3161bc from the CFC-3161bc product mixture; and reducing the purified CFC-3161bc with hydrogen in the presence of catalytic amounts of a hydrogenation catalyst under conditions suitable to produce an HFC-356pecq product mixture.

CFC-1113 is a commercially available material. The telogens useful to telomerize the CFC-1113 in the processes of the invention are of the formula $SO_2Cl_aBr_bI_c$ wherein a=0-2, b=0-2, c=0-2, and a+b+c=2. These telogens are commercially available or may be prepared by the catalytic combination of sulfur dioxide with a suitable halogen. Preferably, the telogen used is sulfuryl chloride, which telogen is commercially available.

Generally, an effective amount of telogen is used, which amount is an amount sufficient to produce telomeric materials containing halogen terminal groups Generally, a mole ratio of CFC-1113 to telogen of from about 1:1 to about 1:25, preferably from about 1:1 to about 1:10, more preferably from about 1:2 to about 1:4 is used.

Telomerization of the CFC-1113 is carried out in the presence of a solvent of the formula $C_4Cl_4F_6$. Telomerization of CFC-1113 in the presence of the solvent carbon tetrachloride is known, but the use of this solvent results in a poor selectivity for CFC-3161bc. It has been discovered that using a solvent of the formula $C_4Cl4F_6$ in the telomerization of CFC-1113 produces CFC-3161bc in high selectivity. This discovery was unexpected because solvents are believed to be inert and not to materially alter the telomerization of CFC-1113.

Suitable solvents of the formula $C_4Cl_4F_6$ include, without limitation, CFC3161bc, 1,1,4,4-tetrachlorohexafluorobutane, 2,2,3,3-tetrachlorohexafluorobutane, and 1,2,3,4-tetrachlorohexafluorobutane. Preferably, the solvent is CFC-3161bc. CFC-3161bc and 2,2,3,3-tetrachlorohexafluorobutane are commercially available. CFC-1113 may be telomerized with carbon tetrachloride to form a mixture of CFC-316 isomers, including 1,1,4,4-tetrachlorohexafluorobutane and 1,2,3,4-tetrachlorohexafluorobutane in significant quantities.

An effective amount of solvent is used in the telomerization of CFC-1113, which amount is an amount capable of dissolving the CFC-1113 and the telogen. Generally, the mole ratio of solvent to CFC-1113 used is from about 1:1 to about 5:1, preferably from about 2:1 to about 4:1.

An initiator also is used in the telomerization reaction. The initiator may be an aromatic peroxide, a chlorinated aromatic peroxide, an aliphatic peroxide, a chlorinated aliphatic peroxide, azoisobutyronitrile, or the like, which initiators are commercially available. Examples of the peroxide initiators include, without limitation, benzoyl peroxide, dichlorobenzoyl peroxide, di-t-butyl peroxide, and trichloroacetyl peroxide. Preferably, benzoyl peroxide is used. Generally, the mole ratio of CFC-1113 to initiator is from about 50:1 to about 500:1, preferably from about 100:1 to about 200:1.

Because water reacts with the telogens, it is preferred to carry out the telomerization reaction under substantially anhydrous conditions. The telomerization may be carried out in any pressure reactor or autoclave that is resistant to the corrosive effects of hydrogen chloride, sulfur dioxide, and sulfuric acid and that can withstand the reaction pressures at which the reaction is run Suitable reactors include, without limitation, those constructed of MONEL™, INCONEL™, HASTELLOY™ as well as glass-lined reactors.

The telomerization reaction temperature, generally, is from about 0° to about 200° C., preferably from about 50° to about 120° C. Reaction times may be from about 1 to about 8 hours, preferably from about 2 to about 6 hours. The pressure at which the telomerization reaction is run is not critical and may vary depending on the quantity of CFC-1113 used, sulfur dioxide generated, and conversion of CFC-1113 to telomers. Convenient operating pressures range from about 50 psig to about 400 psig.

As the telomerization reaction proceeds, a maximum pressure is reached that subsequently subsides. When the pressure drop ceases, the heat is discontinued and purified CFC-3161bc may be recovered from the CFC-3161bc product mixture produced. The volatile materials from the resulting CFC-3161bc product mixture, such as unreacted CFC-1113 and sulfur dioxide, are bled from the reactor. The volatile materials may be fractionated by any convenient method. Excess telogen from the CFC-3161bc product mixture also may be removed, for example by distillation, and recovered for reuse. Any residual acidic impurities in the CFC-3161bc product mixture may then be removed by treatment with an aqueous caustic solution and pure CFC-3161bc recovered by drying and redistillation.

The purified CFC-3161bc undergoes catalytic reduction to produce a HFC-356pecq product mixture. Any suitable reduction catalyst may be used. However, powders are not preferred if the reduction is carried out in the vapor phase because the powders have sufficiently small particles to be carried through the reactor resulting in large pressure drops. Accordingly, for vapor phase reductions, the catalyst preferably is a shaped catalyst.

The reduction catalysts suitable for use include, without limitation, Group VIII metal catalysts such as palladium, platinum, ruthenium, rhodium, iridium, and mixtures thereof. Preferably the catalyst is palladium. The catalyst be supported on any inert support material including, without limitation, alumina or carbon. The catalyst material may be deposited on the support in any convenient form such as the halide or oxide of the catalyst material. Typically, the desired halide or oxide salt is impregnated on the support, dried, and then reduce to the metal with hydrogen. The catalysts useful in the invention are all commercially available.

A catalytic amount of catalyst is used which amount is an amount capable of catalyzing the reduction of CFC-3161bc. For unsupported catalyst, generally, from about 0.5 to about 50, preferably from about 0.5 to about 10 weight percent of catalyst with respect to the organics is used. For supported catalysts, generally loadings of about 0.5 to about 10, preferably from about 0.5 to about 2.5, weight percent of metal with respect to the total weight of the catalyst is used.

Based on reaction stoichiometry, the useful molar ratio of hydrogen to organics used for the reduction reaction is at least about 4:1. Preferably, the ratio is about 4:1 to about 16:1.

The CFC-3161bc reduction reaction temperature generally ranges from about 150° to about 260° C., preferably from about 180° to about 220° C. Conditions for the reaction may vary depending, in part, on catalyst activity which in turn depends on the catalyst selected, the catalyst concentration on the support, and the contact or residence time in the reactor. Residence times may be adjusted by changing the reaction temperature, the catalyst volume, and the flow rates of hydrogen and/or organics. Useful contact times range from about 5 to about 50 seconds, preferably from about 10 to about 20 seconds.

The resulting HFC-356pecq product resulting from the reduction of CFC-3161bc may be recovered from the BFC-356pecq product mixture by any convenient separation or purification method. The invention will be clarified further by a consideration of the following non-limiting examples.

EXAMPLES

Example 1

A 600 mL MONEL™ autoclave equipped with a magnetic stirrer drive was flushed with nitrogen and sequentially charged with 61.0 g CFC-3161bc (0.2 moles), 0.24 g benzoyl peroxide (0.001 mole) and 40.5 sulfuryl chloride (0.3 mole). The autoclave was closed, cooled to −25° C., evacuated and then charged with 18.2 g CFC-1113 (0.156 mole). The reaction mixture was heated with stirring to about 95° C. over 40 min and maintained at that temperature for an additional 4 hours. During this period, a maximum gauge pressure of 100 psig was reached and then slowly subsided to 75 psig. At the end of the telomerization reaction, the reactor was cooled to 0° C. and the volatile materials were bled from the system to give 114.0 g liquid product (95% recovery), which product was transferred to a distilling pot, heating the liquid product mixture to a pot temperature of 110° C. at atmospheric pressure gave 22.0 g distillate and 78.0 g pot residue. GC analysis, area percentages, of the distillate and residue indicated: $SO_2Cl_2$ (84.1%); CFC-3161bc (6.8%), CFC-1113 (7.0%); $C_6$ telomers and high boilers (0.5%) for the distillate and for the residue CFC-3161bc (85.2%), CFC-316 isomers (9.7%); $SO_2Cl_2$ (0.6%); $C_6$ telomers (1.9%) and high boilers (0.9%). GC-MS of the pot residue showed: base peak 101 $(CFCl_2)^+$; 85 $(CF_2Cl)^+$; 267 $(M-Cl)^+$; 69 $(CF_3)$; 151 $(CF_2CFCl_2)^+$; and 135 $(M^+ - C_2F_2Cl_3)$.

Comparative Example 1

The procedure of Example 1 was used. 154.0 g carbon tetrachloride (1.0 mole), 3.5 g benzoyl peroxide (0.015 mole), and 33.3 g sulfuryl chloride (0.25 mole) were charged to the autoclave which was closed, cooled to −25° C., evacuated, and then charged with 28.2 g CFC-1113 (0.24 mole). The reaction mixture was heated with stirring to approximately 95° C. over 40 min. and maintained at that temperature for an additional 4 hours. During this period, a maximum gauge pressure of 180 psig was reached which slowly subsided to 140 psig. At the end of the telomerization reaction, the reactor was cooled to 0° C. and the volatile materials bled from the system gave 212.0 g liquid product, a 97% recovery, that was transferred to a distilling pot. Unreacted starting materials and carbon tetrachloride were boiled off to give 35.3 g of residue that was analyzed by GC. The analysis showed: $CCl_4$ (20%); CFC-316 isomers (34%); chlorobenzene (12.3%); C3 isomers (2.0%); $C_6$ and high boilers (28.0%). GC-MS of the residue showed: $CCl_4$; chlorobezene; $CFCl_2CF_2CFClCF_2Cl$; $CFCl_2CF_2CF_2CFCl_2$; $CCl_3CFClCF_2Cl$; $CCl_3CF_2CFCl_2$; $C_6Cl_5F_9$; $C_8Cl_6F_{12}$; and $C_{10}Cl_7F_{15}$.

Example 1 and Comparative Example 1 demonstrate that using the CFC-1113 telomerization process of the invention produces CFC-3161bc with good selectivity.

Example 2

A 600 mL MONEL™ autoclave equipped with a magnetic stir drive was flushed with nitrogen and then sequentially charged with 45.8 g CFC-3161bc (0.15 mole), 0.25 g benzoyl peroxide (0.001 mole), and 83.0 g sulfuryl chloride (0.62 mole). The autoclave was closed, cooled to −25° C., evacuated and then charged with 18.2 g chlorotrifluoroethylene (0.156 mole). The reaction mixture was heated with stirring to about 105° C. over 30 min and maintained at that temperature for an additional 4 hrs. During this period, a maximum gauge pressure of 105 psig was reached and then slowly subsided to 90 psig. At the end of the telomerization reaction, the reactor was cooled to 0° C. and the volatile materials were bled from the system to give 139.6 g liquid product, 95% recovery, which was transferred to a distilling pot. Heating the liquid product mixture to a pot temperature of 100° C. at atmospheric pressure gave 51.2 g distillate and 74.3 g pot residue. GC analysis in area percentages of the distillate and pot residue indicated: CFC-3161bc (93.8%), other CFC-316 isomers (1.0%), $SO_2Cl_2$ (0.1%), $C_6$ telomers (1.7%), and high boilers (0.4%) in the pot residue; and $SO_2Cl_2$ (95.1%), CFC-3161bc (0.9%), chlorotrifluoroethylene (1.1%), $C_6$ telomers and high boilers (0.4%) in the distillate.

Example 3

A 600 mL MONEL™ autoclave equipped with a magnetic stir drive was flushed with nitrogen and then sequentially charged with 22.8 g CFC-3161bc (0.075 mole), 0.24 g benzoyl peroxide (0.001 mole), and 83.4 g sulfuryl chloride (0.62 mole). The autoclave was closed, cooled to −25° C., evacuated and then charged with 18.7 g chlorotrifluoroethylene (0.161 mole). The reaction mixture was heated with stirring to about 75° C. over 30 min and maintained at that temperature for an additional 4 hrs. During this period, a maximum gauge pressure of 50 psig was reached and then slowly subsided to 45 psig. At the end of the telomerization reaction, the reactor was cooled to 0° C. and the volatile materials were bled from the system to give 119.9 g liquid product, 96% recovery, which was transferred to a distilling pot. Heating the liquid product mixture to a pot temperature of 100° C. at atmospheric pressure gave 63.2 g distillate and 39.9 g pot residue. GC analysis in area percentages of the distillate and pot residue indicated: CFC-3161bc (89.7%), other CFC-316 isomers (0.7%), $SO_2Cl_2$ (0.1%), $C_6$ telomers (4.7%), $C_8$ telomers (1.9%), and high boilers (0.6%) in the pot residue; and $SO_2Cl_2$ (86.4%), CFC-3161bc (4.2%), chlorotrifluoroethylene (8.2%), $C_6$ telomers and high boilers (0.9%) in the distillate.

Example 4

A 600 mL MONEL™ autoclave equipped with a magnetic stir drive was flushed with nitrogen and then sequentially charged with 22.8 g CFC-3161bc (0.075 mole), 0.24 g benzoyl peroxide (0.001 mole), and 21.0 g sulfuryl chloride (0.156 mole). The autoclave was closed, cooled to −25° C., evacuated and then charged with 18.0 g chlorotrifluoroethylene (0.155 mole). The reaction mixture was heated with stirring to about 105° C. over 30 min and maintained at that temperature for an additional 4 hrs. During this period, a maximum gauge pressure of 80 psig was reached and then slowly subsided to 75 psig. At the end of the telomerization reaction, the reactor was cooled to 0° C. and the volatile materials were bled from the system to give 50.1 g liquid product, 81% recovery, which was transferred to a distilling pot. Heating the liquid product mixture to a pot temperature of 100° C. at atmospheric pressure gave 37.2 g distillate and 3.0 g pot residue. GC analysis in area percentages of the distillate and pot residue indicated: CFC-3161bc (89.7%), other CFC-316 isomers (1.3%), $SO_2Cl_2$ (0.9%), $C_6$ telomers (3.3%), $C_8$ telomers (1.3%), and high boilers (0.7%) in the pot residue; and $SO_2Cl_2$ (96.7%), CFC-3161bc (0.1%), chlorotrifluoroethylene (3.0%), $C_6$ telomers and high boilers (0.1%) in the distillate.

Example 5

A 600 nL MONEL™ autoclave equipped with a magnetic stir drive was flushed with nitrogen and then sequentially charged with 45.8 g CFC-3161bc (0.15 mole), 0.24 g benzoyl peroxide (0.001 mole), and 21.0 g sulfuryl chloride (0.156 mole). The autoclave was closed, cooled to −25° C., evacuated and then charged with 20.7 g chlorotrifluoroethylene (0.18 mole). The reaction mixture was heated with stirring to about 72° C. over 30 min and maintained at that temperature for an additional 4 hrs. During this period, a maximum gauge pressure of 100 psig was reached and then slowly subsided to 95 psig. At the end of the telomerization reaction, the reactor was cooled to 0° C. and the volatile materials were bled from the system to give 78.9 g liquid product, 90% recovery, which was transferred to a distilling pot. Heating the liquid product mixture to a pot temperature of 100° C. at atmospheric pressure gave 2.8 g distillate and 64.8 g pot residue. GC analysis in area percentages of the distillate and pot residue indicated: CFC-3161bc (78.1%), other CFC-316 isomers (5.3%), $SO_2Cl_2$ (0.6%), $C_6$ telomers (3.6%), $C_8$ telomers (3.6%), and high boilers (4.9%) in the pot residue; and $SO_2Cl_2$ (97.3%), CFC-3161bc (0.5%), chlorotrifluoroethylene (0.4%), $C_6$ telomers and high boilers (0.2%) in the distillate.

Example 6

The reactor used was a vertical 1" internal diameter MONEL™ tube with electrical tape on the outside. A MONEL™ thermocouple measured the inside tube temperature and the tube was packed with 50 cc of 0.5% Pd/alumina as $\frac{1}{8}$" pellets mixed with 50 cc borosilicate glass helices for a total bed volume of 100 cc. The rest of the reactor was packed with 170 cc of glass beads. Hydrogen flow rate was maintained at 140 cc/min and organic material was fed through the top of the reactor using a syringe pump. The flow rate of organic material was maintained at 7.0 g/h. Effluent from the reactor was condensed in two −78° C. cold traps the organic flow was started at an initial temperature of 205° C. and maintained between 203°–222° C. for five hours. After a total time of 3 h 5 min, 21.0 g of CFC-3161bc and other 316 isomers had been fed through the reactor. The cold traps contained 7.3 g material. Analysis of the crude material by GC-MS area percentages showed: $CF_2HCFHCF_2CFH_2$ (HFC-356pecq); $CF_2ClCFHCF_2CFH_2$; $C_4H_3F_6Cl$; $CF_3CF_2CBFCH_3$ $C_4H_6F_4$; and $C_4H_5F_5$.

Example 7

The procedure of Example 2 is used. 11.7 g (0.1 mole) CFC-1113 are added to a mixture of 30.4 g CFC-3161bc (0.0 mole), 0.17 g benzoyl peroxide (0.0007 mole), and 55.3 g sulfuryl chloride (0.41 moles) in a 600 mL MONEL™ autoclave and the resultant mixture is heated to 105° C. in 30 minutes and maintained at that temperature for 4 hours with stirring. After work-up and distillation, 50.0 g pot residue is subjected to reduction at 200°–220° C. as described in Example 6, 17.5 g material is collected in the cold traps and GC-MS analysis of that material indicates the presence of $CF_2HCFHCF_2CFH$ (HFC-356pecq), $CF_2ClCFHCF_2CFH_2$, $C_4H_3F_6Cl$, $CF_3CF_2CHFCH_3C_4H_6F_4$, and $C_4H_5F_6$.

What is claimed is:

1. A process for preparing 1,1,2,3,3,4-hexafluorobutane comprising the steps of:

telomerizing chlorotrifluoroethylene in the presence of effective amounts of a telogen, a solvent of the formula $C_4Cl_4F_6$ and an initiator under conditions suitable to produce a 1,1,3,4-tetrachlorohexafluorobutane product mixture;

recovering 1,1,3,4-tetrachlorohexafluorobutane from the 1,1,3,4-tetrachlorohexafluorobutane product mixture;

reducing 1,1,3,4-tetrachlorohexafluorobutane with hydrogen in the presence of a reduction catalyst selected from the group consisting of palladium, platinum, ruthenium, rhodium, iridium, and mixtures thereof under conditions suitable to produce a product mixture comprising 1,1,2,3,3,4-hexafluorobutane.

2. The process of claim 1 wherein the solvent is selected from the group consisting of 1,1,3,4-tetrachlorohexafluorobutane, 1,1,4,4-tetrachlorohexafluorobutane, 2,2,3,3-tetrachlorohexafluorobutane, and 1,2,3,4-tetrachlorohexafluorobutane.

3. The process of claim 1 wherein the solvent is 1,1,3,4-tetrachlorohexafluorobutane.

4. The process of claim 1 wherein the telogen is of the formula $SO_2Cl_aBr_bI_c$ wherein a=0-2, b=0-2, c=0-2, and a+b+c=2.

5. The process of claim 1 wherein the telogen is sulfuryl chloride.

6. The process of claim 1 wherein the initiator is selected from the group consisting of aromatic peroxide, chlorinated aromatic peroxide, aliphatic peroxide, chlorinated aliphatic peroxide, and azoisobutyronitrile.

7. The process of claim 1 wherein the initiator is benzoyl peroxide.

8. A process for preparing 1,1,2,3,3,4-hexafluorobutane comprising the steps of:

preparing 1,1,3,4-tetrachlorohexafluorobutane by telomerizing chlorotrifluoroethylene in the presence of a telogen present in a mole ratio of chlorotrifluoroethylene to telogen of about 1:1 to about 1:25, a solvent of the formula $C_4Cl_4F_6$ present in a mole ratio of solvent to chlorotrifluoroethylene of about 1:1 to about 5:1, and an initiator at a temperature of about 0° to about 200° C. to produce a 1,1,3,4-tetrachlorohexafluorobutane mixture;

recovering 1,1,3,4-tetrachlorohexafluorobutane from the 1,1,3,4-tetrachlorohexafluorobutane product mixture;

reducing 1,1,3,4-tetrachlorohexafluorobutane with hydrogen in the presence of a reduction catalyst selected from the group consisting of palladium, platinum, ruthenium, rhodium, iridium, and mixtures thereof under conditions suitable to produce a 1,1,2,3,3,4-hexafluorobutane product mixture comprising 1,1,2,3,3,4-hexafluorobutane.

9. The process of claim 8 wherein the solvent is selected from the group consisting of 1,1,3,4-tetrachlorohexafluorobutane, 1,1,4,4-tetrachlorohexafluorobutane, 2,2,3,3-tetrachlorohexafluorobutane, and 1,2,3,4-tetrachlorohexafluorobutane.

10. The process of claim 8 wherein the solvent is 1,1,3,4-tetrachlorohexafluorobutane.

11. The process of claim 8 wherein the telogen is of the formula $SO_2Cl_aBr_bI_c$ wherein a=0-2, b=0-2, c=0-2, and a+b+c=2.

12. The process of claim 8 wherein the telogen is sulfuryl chloride.

13. The process of claim 8 wherein the initiator is selected from the group consisting of aromatic peroxide, chlorinated aromatic peroxide, aliphatic peroxide, chlorinated aliphatic peroxide, and azoisobutyronitrile.

14. The process of claim 8 wherein the initiator is benzoyl peroxide.

15. A process for preparing 1,1,2,3,3,4-hexafluorobutane comprising the steps of:

preparing 1,1,3,4-tetrachlorohexafluorobutane by telomerizing chlorotrifluoroethylene in the presence of a telogen of the formula $SO_2Cl_aBr_bI_c$ wherein a=0-2, b=0-2, c=0-2, and a+b+c=2 present in a mole ratio of chlorotrifluoroethylene to telogen of about 1:1 to about 1:25, a solvent selected from the group consisting of 1,1,3,4-tetrachlorohexafluorobutane, 1,1,4,4-tetrachlorohexafluorobutane, 2,2,3,3-tetrachlorohexafluorobutane, and 1,2,3,4tetrachlorohexafluorobutane present in a mole ratio of solvent to chlorotrifluoroethylene of about 1:1 to about 5:1, and an initiator at a temperature of about 0° to about 200° C. to produce a 1,1,3,4-tetrachlorohexafluorobutane mixture;

recovering 1,1,3,4-tetrachlorohexafluorobutane from the 1,1,3,4-tetrachlorohexafluorobutane product mixture; and reducing 1,1,3,4-tetrachlorohexafluorobutane with hydrogen in the presence of a reduction catalyst selected from the group consisting of palladium, platinum, ruthenium, rhodium, iridium, and mixtures thereof under conditions suitable to produce a 1,1,2,3,3,4-hexafluorobutane product mixture comprising 1,1,2,3,3,4-hexafluorobutane.

16. The process of claim 15 wherein the solvent is 1,1,3,4-tetrachlorohexafluorobutane.

17. The process of claim 16 wherein the telogen is sulfuryl chloride.

18. The process of claim 15 wherein the initiator is selected from the group consisting of aromatic peroxide, chlorinated aromatic peroxide, aliphatic peroxide, chlorinated aliphatic peroxide, and azoisobutyronitrile.

19. The process of claim 15 wherein the initiator is benzoyl peroxide.

* * * * *